United States Patent [19]

Bansal

[11] 4,043,330
[45] Aug. 23, 1977

[54] ARM BOARD FOR INTRAVENOUS INFUSIONS

[76] Inventor: Surinder K. Bansal, Apt. 6, 33 E. Lakeshore Drive, Cincinnati, Ohio 45237

[21] Appl. No.: 659,116

[22] Filed: Feb. 18, 1976

[51] Int. Cl.² ............................................. A61F 13/00
[52] U.S. Cl. .................................. 128/133; 128/87 R; 248/118; 297/411
[58] Field of Search .................. 128/133, 87 R, 87 A, 128/87 B, 87 C, DIG. 6, 214 R, 88, 94, 132 R; 248/118, 22; 297/411, 453; 269/328; 2/267, 268; 5/337, 355, 361 R

[56] References Cited

U.S. PATENT DOCUMENTS

| 2,763,264 | 9/1956 | McInnerny | 128/133 |
| 3,059,636 | 10/1962 | Schwartz | 128/133 |
| 3,374,785 | 3/1968 | Gaylord | 128/87 R X |
| 3,556,092 | 1/1971 | Eisenberg | 128/87 R |
| 3,695,258 | 10/1972 | Castle | 128/87 R |
| 3,850,167 | 11/1974 | Seeley | 128/87 R |
| 3,886,942 | 6/1975 | Bernardin | 128/290 R |

Primary Examiner—Robert W. Michell
Assistant Examiner—Michael H. Thaler
Attorney, Agent, or Firm—Oliver E. Todd, Jr.

[57] ABSTRACT

An improved medical restraining board for temporarily restraining, for example, a patient's forearm and wrist during intravenous administration of fluids. The arm board includes an elongated flat rigid support member which is padded on at least one side with a substantially flat sheet of flexible material having a plurality of spaced enclosed gas-filled pockets formed therein. The support member and padding are enclosed within an outer cover formed from a porous hydrophobic material, preferably of porous spun-bonded polyethylene fibers. In a modified embodiment, the support member and padding are enclosed within a microporous sealed inner cover and the outer cover is disposable and has a moisture-absorbent lining.

5 Claims, 4 Drawing Figures

U.S. Patent  Aug. 23, 1977  4,043,330
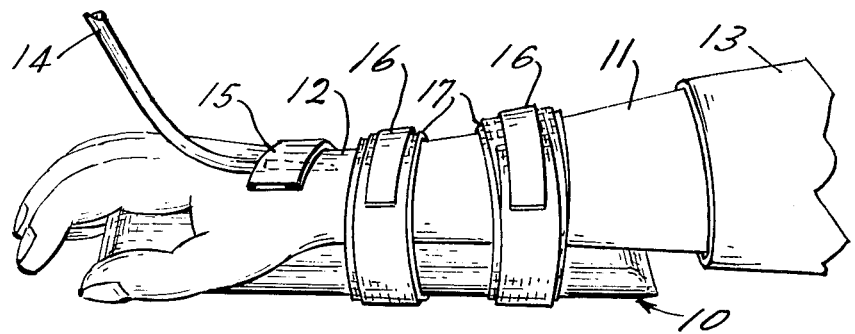
FIG-1-
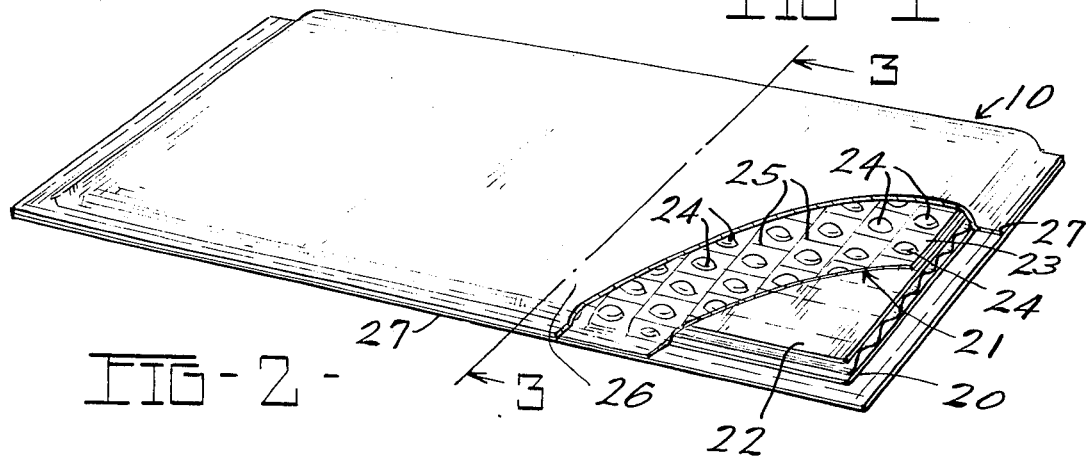
FIG-2-
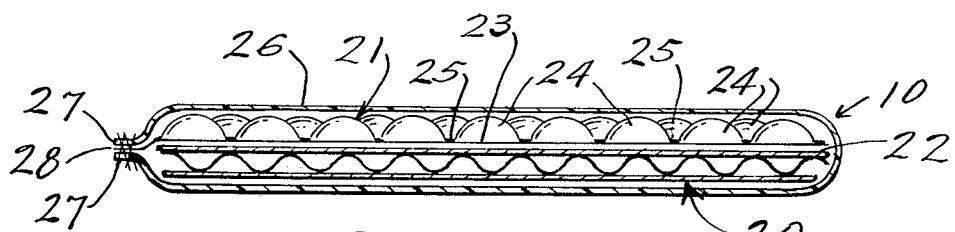
FIG-3-
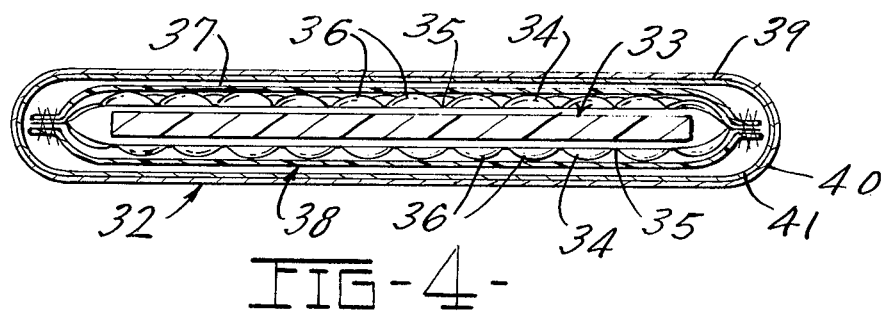
FIG-4-

ARM BOARD FOR INTRAVENOUS INFUSIONS

BACKGROUND OF THE INVENTION

This invention relates to restraints and more particularly to an improved board for restraining the forearm and wrist of a patient.

Padded arm boards are commonly used in hospitals for various purposes. When, for example, fluids are administered intravenously through a cannula inserted through the back of a patient's hand and into a vein, the patient's forearm and wrist may be restrained with an arm board to prevent the patient from moving his forearm and wrist. Arm boards are also used as a temporary splint in emergency situations to support injured limbs. Both disposable and reusable arm boards are commercially available for use by doctors and hospitals. One type of disposable arm board is formed from a rigid expanded synthetic resinous material, such as Styrofoam. When a molded Styrofoam arm board is used on a patient, it has an advantage in that tape attaching it to the patient may be removed and replaced without damage to the arm board. Furthermore, such arm board is relatively inexpensive. However, Styrofoam and similar expanded synthetic resinous materials are good insulating materials and, as a consequence, may be uncomfortable for the patient due to heat buildup. Moisture is also retained between the patient's skin and the arm board which further adds to the patient's discomfort.

A typical reusable arm board is disclosed in U.S. Pat. No. 3,059,636 which issued on Oct. 23, 1962. The arm board disclosed in this patent consists of a rigid base member having resilient padding positioned on one side. The padding and base member are sealed within a nonporous vinyl cover. A disposable paper sleeve is then placed over the vinyl cover while the arm board is used with a patient. The sleeve is replaced whenever the arm board is used with a new patient to prevent cross-infection. The disposable paper sleeve must also be replaced each time the arm board is removed from a patient, even though it is reattached to the same patient. This is because the disposable paper cover is sufficiently weak as to tear whenever tape used to attach it to the patient is removed. Another difficulty with an arm board of this type is caused by moisture present on a patient's skin. If the disposable paper cover is made nonabsorbent, excessive moisture present on a patient's skin may cause considerable discomfort for the patient. On the other hand, if the disposable cover is made from a moisture-absorbent paper, absorbed moisture may further weaken the cover and cause it to tear. The absorbed moisture may also cause discomfort for the patient.

SUMMARY OF THE INVENTION

According to the present invention, an improved medical restraining board is provided for temporarily restraining a patient's forearm and wrist during intravenous administration of fluids and also for temporarily restraining sprained or broken limbs such as an arm, a wrist, an ankle and the like. The restraining board of the present invention includes an elongated flat rigid base member which is padded on at least one side with a substantially flat sheet of flexible material having a plurality of spaced enclosed gas-filled pockets or bubbles formed therein. The rigid member and padding are then enclosed within an outer envelope formed from a porous nonabsorbent material, preferably a porous material formed from bonded spun fibers of polyethylene or a similar polyolefin material. For disposable restraining boards, the rigid base member is made from an inexpensive rigid material, for example, from corrugated cardboard. In a modified embodiment where the restraining board is to be reusable, the rigid base member is made from a more permanent material such as wood or bonded wood particle board or from a rigid synthetic resinous material. In such an embodiment, the rigid member and padding are preferably enclosed within a microporous or substantially nonporous sealed inner cover which passes air but not fluids. The porous outer envelope is made in the form of an open-ended case to be disposable and, preferably, is provided with a moisture-absorbent lining. The substantially nonporous inner cover preferably is provided with micropores which permit air passage through the inner envelope while prohibiting the passage of liquids such as water or perspiration. Air passages are also provided between the padding and the enclosing cover. The flexible padding material defines a grid of interconnected, outwardly opening passages between adjacent ones of the spaced pockets. Heat passing through the cover into the portion of the passages immediately adjacent the patient's skin is carried away to provide a cooler, drier and more comfortable restraining board. Perspiration is also carried away either through the interconnected passages in the padding or in the moisture-absorbent lining on the outer cover.

Accordingly, it is an object of the invention to provide an improved arm board for temporarily restraining a patient's forearm and wrist during the administration of fluids intravenously.

Another object of the invention is to provide an improved disposable arm board which is inexpensive and capable of breathing for maintaining a relatively cool and dry surface between the patient's arm and the arm board.

Still another object of the invention is to provide an improved board for temporarily restraining a sprained or broken limb.

Other objects and advantages of the invention will become apparent from the following detailed description, with reference being made to the accompanying drawings.

BRIEF DESCRIPTION OF THE DRAWINGS

FIG. 1 is a side pictorial illustration showing a medical restraining board constructed in accordance with the present invention attached to a patient's forearm and wrist during the administration of fluids intravenously;

FIG. 2 is a fragmentary, perspective view of an improved medical restraining board constructed in accordance with one embodiment of the invention;

FIG. 3 is a cross-sectional view taken along line 3—3 of FIG. 2; and

FIG. 4 is a cross-sectional view of a modified embodiment of the medical restraining board of the present invention.

DESCRIPTION OF THE PREFERRED EMBODIMENTS

Turning now to the drawings and particularly to FIG. 1, an improved medical restraining board 10 constructed in accordance with the present invention is shown attached to restrain the forearm 11 and wrist 12 of a patient 13 during the intravenous administration of fluids through a tube 14. The tube 14 is attached to a conventional cannula which is inserted through the patient's wrist and into a vein and is held in place by means of an adhesive bandage 15. The restraining board 10 is also shown attached to the patient's forearm 11 with two adhesive bandages 16. Prior to wrapping the adhesive bandages 16 around the restraining board 10 and the forearm 11, strips of gauze 17 may be wrapped around the restraining board 10 and forearm 11 for the patient's comfort. The restraining board 10 should be attached to the patient 13 such that it extends from the forearm 11 well under the wrist 12 to restrain the wrist 12 from movement with respect to the forearm 11.

Turning now to FIGS. 2 and 3, details are shown for the restraining board 10 of the present invention. The restraining board 10 has a flat rectangular shape and may be produced in various widths and lengths for use with different size patients and for restraining different portions of the body. To provide rigidity, the restraining board 10 is provided with a flat rigid base member 20. The rigid base member 20 is formed from corrugated cardboard having corrugations running in the longitudinal direction of the board 10 such that they extend substantially parallel to the patient's forearm 11 and wrist 12. When the restraining board 10 is to be disposable, corrugated cardboard is extremely inexpensive and provides sufficient rigidity. However, where the restraining board 10 is to be reused with either the same or a different patient, it may be desirable to provide a more permanent material for the rigid base member 20, such as a thin piece of plywood, particle board, Masonite or a molded rigid synthetic resinous material.

Padding 21 is placed over at least one side 22 of the rigid base member 20. The padding 21 is placed at least on the side 22 of the rigid member 20 which is positioned in contact with the patient to protect the patient and to add to the patient's comfort. The padding 21 is in the form of a substantially flat sheet 23 of flexible synthetic resinous material having a plurality of spaced enclosed gas-filled pockets or bubbles 24 formed therein. The flat sheet 23 is positioned in contact with the rigid base member 20 such that open spaces 25 between adjacent ones of the pockets 24 define a grid of interconnected channels or air passages opening away from the sheet 23 and the rigid base member 20. An outer cover 26 in the form of a flat sheet of fluid pervious hydrophobic material is folded over the padding 21 and the rigid base member 20. The cover 26 has edges 27 which extend past the rigid base member 20. During manufacture of the restraining board 10, the padding 21 is positioned on at least one side of the base member 20 and preferably has an edge 28 which extends between the extended cover edges 27. The extended cover edges 27 and the padding edge 28 are then sealed together by any conventional method, as by heat sealing to fuse the edges 27 and 28 together.

A suitable padding material is commercially available for use as the padding 21 in the restraining board 10 from Sealed Air Corporation of Fair Lawn, N.J. and is sold under the trademark "Aircap". Aircap material consists of a flat sheet of flexible synthetic resinous material having spaced pockets or bubbles projecting from one side in a regular grid or matrix. The interior of the pockets or bubbles is covered with a coating to prevent air leakage.

The material from which the outer cover 26 is constructed is also commercially available. The material for the cover 26 preferably consists of thermally bonded fibers spun from a polyolefin and preferably from polyethylene. The fibers forming the outer cover 26 should be hydrophobic and sufficiently porous as to pass air and moisture from a patient's skin. If the fibers are bonded to a density which is not normally porous, the material forming the cover may be perforated so that it will breathe or pass air and moisture. Such a material is available, for example, from E. I. du Pont de Nemours & Co. under the trademark "Tyvek". Tyvek is a high density material formed from bonded, spun polyethylene fibers which is normally of very low porosity. However, it is available in a style which is perforated to provide porosity. Since the cover 26 is porous, heat and moisture generated between the patient's skin and the adjacent surfaces of the restraining board 10 are dissipated through the porous outer cover 26 and the spaces 25 between the spaced pockets or bubbles 24 in the padding 21. This greatly increases the comfort of the restraining board 10 for the patient 13 over prior art restraining boards such as those molded from polystyrene and similar rigid materials.

Turning now to FIG. 4, a cross-sectional view is shown of a modified restraining board 32 which is adapted to be reusable. Since the restraining board 32 is reusable, it is provided with a base member 33 which is of a strong rigid material, such as a rigid synthetic resinous material, wood, particle board, Masonite and the like. The base member 33 is covered with padding 34 on at least one side (shown on both sides in FIG. 4). The padding 34 is preferably Aircap, or a similar material, which consists of a flat sheet 35 of a flexible synthetic resinous material having a plurality of sealed, air-filled pockets or bubbles 36 spaced in a regular grid or matrix pattern. The rigid base member 33 and padding 34 is enclosed within an inner envelope or cover 37 formed from a nonabsorbent microporous material. Preferably, the micropores in the material are such as to pass air for cooling the patient's skin yet not to pass liquids which might eventually contaminate the restraining board 32. The inner envelope 37 may be formed, for example, from a nonporous or microporous material formed from bonded, spun fibers of polyethylene or other polyolefin such as the commercially available Tyvek in a non-perforated style. The inner portion 38 of the restraining board 32 consisting of the envelope 37, the padding 34 and the base member 33 is reusable. Since the envelope 37 is, at most, microporous and will not pass liquids, the inner portion 38 may be cleaned so as not to cause cross infection between successive patients. During use, the inner portion 38 of the restraining board 32 is enclosed within a disposable outer cover 39 which has a liquid and air pervious hydrophobic outer layer 40 of a perforated or porous Tyvek material, or of a similar material, and a highly absorbent inner layer or lining 41. The lining 41 may, for example, be of a moisture-absorbent paper type material. The outer layer 40 not only remains dry to the patient's touch to prevent irritation, but it also breathes. In addition, the outer layer 40 strengthens the cover 39 to permit removing and reattaching adhesive tape when the restraining board 32 is temporarily removed and reattached to a patient. The outer cover 39 is intended to be disposable and may be made in the form of an open-ended envelope which slips over the inner board portion 38.

Various modifications and changes may be made in the above-described preferred embodiments of the restraining board of the present invention. For example, various types of commercially available materials may be used for the outer cover in addition to the exemplary Tyvek. However, the material forming the outer cover should be hydrophobic and sufficiently porous to allow enough air circulation around the portion of a patient's skin in contact with the cover such that the skin remains dry. Although the padding is preferably of a material such as Aircap, it may be formed from other materials such as urethane foam or polyethylene foam in a modified embodiment of the restraining board. In such case, the outer surface of the padding is shaped to define outwardly opening interconnected channels so that the resilient board will "breathe". Furthermore, the material used for the rigid base member is not critical so long as the base member has sufficient rigidity. Cardboard is a suitable rigid base material for a disposable medical restraining board. For reusable restraining boards, more permanent materials such as hard synthetic resins, wood, particle board and the like may be more desirable. It should also be appreciated that the intended use for the restraining board of the present invention is not limited to restraining the forearm and wrist of a patient during the intravenous administration of fluids. The board may also be used for temporarily restraining the forearm or wrist of a patient which has been sprained or broken or for temporarily restraining other portions of a patient's body, such as the elbow, a leg, or an ankle.

What I claim is:

1. A medical restraining board comprising, in combination, a flat rigid support member having two opposed sides, means padding at least one side of said support member, said padding means including a generally flat sheet of resilient material having a plurality of spaced enclosed gas-filled pockets formed therein and wherein spaces between said pockets define a plurality of interconnected outwardly opening air-filled channels, a fluid pervious hydrophobic outer cover enclosing said support member and said padding, said outer cover being removable from said support member and padding, a microporous hydrophobic inner cover permanently enclosing said support member and padding, said inner cover being formed from a gas pervious and liquid impervious material, and moisture absorbing means positioned between said outer cover and said inner cover.

2. A medical restraining board, as set forth in claim 1, wherein said moisture absorbing means comprises a moisture absorbing paper lining bonded to the inside of said outer cover.

3. A medical restraining board, as set forth in claim 2, wherein said inner and outer covers are of spun bonded polyethylene fibers and wherein said outer cover is perforated.

4. A medical restraining board comprising, in combination, a flat rigid support member having two opposed sides, means padding at least one side of said support member, said padding means defining a plurality of interconnected outwardly opening air-filled channels, a fluid pervious hydrophobic outer cover enclosing said support member in said padding, said outer cover being removable from said support member and padding, and a microporous hydrophobic inner cover permanently enclosing said support member and padding, said inner cover being formed from a gas pervious and liquid impervious material, and moisture absorbing means positioned between said outer and said inner cover.

5. A medical restraining board, as set forth in claim 4, wherein said moisture absorbing means comprises a moisture absorbing paper bonded to the inside of said outer cover.

* * * * *